US00PP36820P3

(12) United States Plant Patent
Olesen

(10) Patent No.: US PP36,820 P3
(45) Date of Patent: Jul. 15, 2025

(54) ROSE PLANT NAMED 'Poulpah124'

(50) Latin Name: *Rosa hybrida*
Varietal Denomination: Poulpah124

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,187

(22) Filed: Sep. 5, 2024

(65) Prior Publication Data

US 2025/0107473 P1 Mar. 27, 2025

(30) Foreign Application Priority Data

Sep. 22, 2023 (QZ) ..... PBR 20231976

(51) Int. Cl.
*A01H 5/02* (2018.01)
*A01H 6/74* (2018.01)

(52) U.S. Cl.
USPC ..... Plt./119
CPC ..... *A01H 6/749* (2018.05)

(58) Field of Classification Search
USPC ..... Plt./116, 118, 119
See application file for complete search history.

(56) References Cited

U.S. PATENT DOCUMENTS

PP25,970 P3 * 10/2015 Olesen ..... A01H 5/02
Plt./116

* cited by examiner

*Primary Examiner* — Susan McCormick Ewoldt
*Assistant Examiner* — Zachariah Allan Kay

(57) ABSTRACT

A new garden rose plant of the Miniature class which has abundant, yellow and red-purple striped flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah124'.

This application claims priority to Plant Breeder's Rights Application Number 2023/1976, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah124', originated as a single seedling from the stated cross.

The new variety may be distinguished from its male pollen parent and female seed parent primarily by the following characteristics. The male pollen parent plant has pink and white striped flowers while the new variety has yellow and red-purple striped flowers. The female seed parent plant has yellow flowers while the new variety has yellow and red-purple striped flowers.

The objective of the hybridization of this rose variety was to create a new and distinct variety with unique qualities, such as:

1. Uniform and abundant yellow and red-purple striped flowers;
2. Vigorous, but compact growth when propagated on its own roots;
3. Exceptional disease resistance.

This combination of qualities is not present in previously available commercial cultivars of this type, known to the inventor, and distinguish 'Poulpah124' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah124' was selected in the spring of 2016 by the inventor as a single plant from the progeny of the aforementioned hybridization.

Asexual reproduction of 'Poulpah124' by rooted cuttings was first done by Mogens N. Olesen in the nursery in Fredensborg, Denmark in July 2016. This initial and other subsequent asexual propagations conducted in controlled environments have demonstrated that the characteristics of 'Poulpah124' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah124'.

Specifically illustrated in FIG. 1 of the drawings are open flowers viewed from above and the side, flower bud, petals detached revealing reproductive flower parts.

Figure 1:
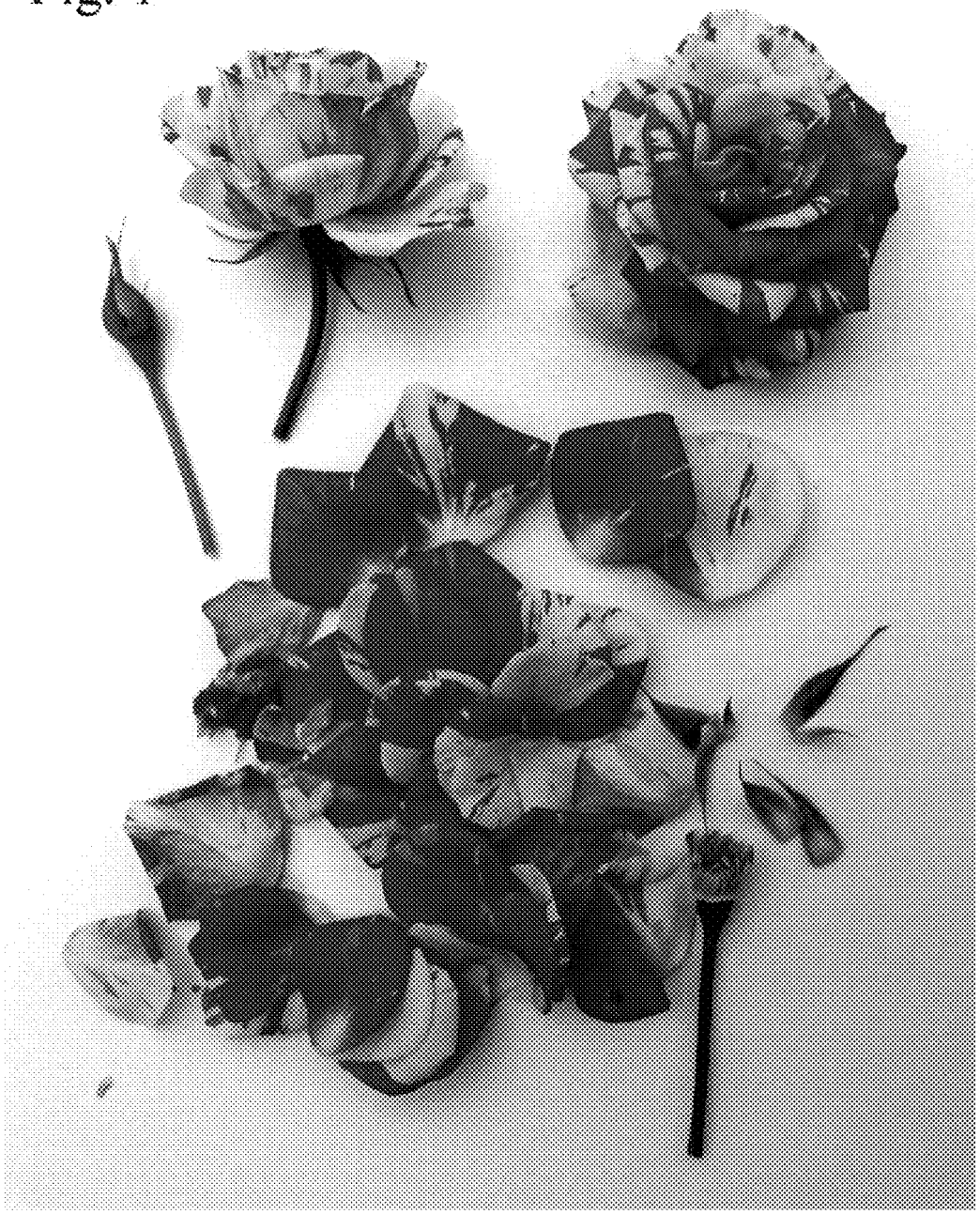
Figure 2:
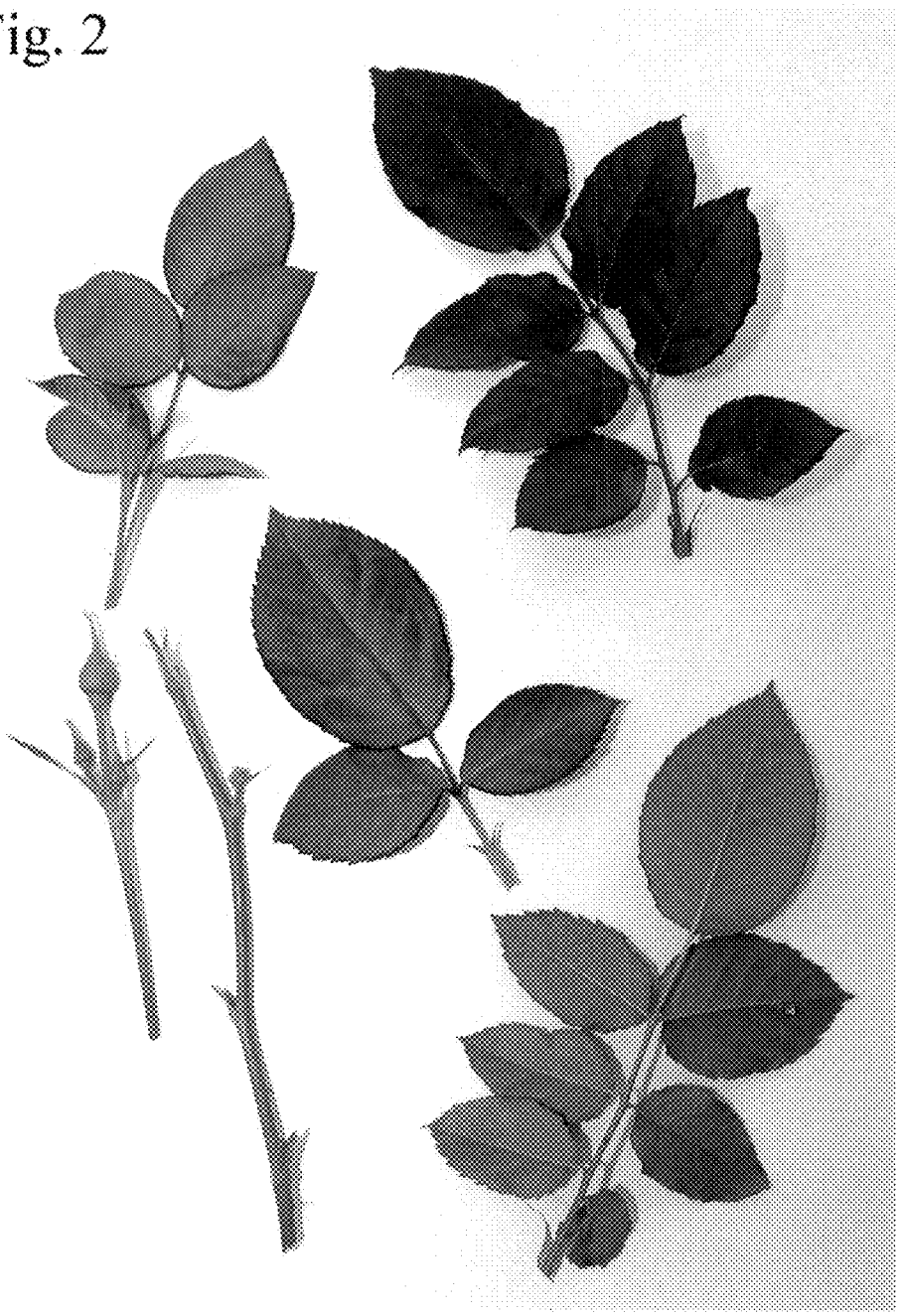

Specifically illustrated in FIG. 2 of the drawings are bare stem, juvenile leaves, and mature leaves. Plants shown are 3 months old.

DETAILED DESCRIPTION OF THE VARIETY

The following is a description of 'Poulpah124', as observed in its growth in a glasshouse nursery in Odense Denmark. Observed plants are 3 months of age, and were grown on their own roots in 15 cm pots. Color references are made using The Royal Horticultural Society (London, England) Colour Chart, 2001, except where common terms of color are used.

For a comparison, several physical characteristics of the rose variety 'Poulpah068', U.S. Plant Pat. No. 25,970 are compared to the claimed plant. While 'Poulpah124' has 55 flower petals, 'Poulpah068' has 20 flower petals. The claimed plant has strong perfume while 'Poulpah068' does not. Open flowers of 'Poulpah124' are generally Yellow Group 8C and Red-Purple Group 58B in color while 'Poulpah068' has a general tonality of Red Group 52A and 52C splashed with White Group N155B.

FLOWER AND FLOWER BUD

Blooming habit: Continuous.

Flower bud:

- *Size*.—Upon opening, 21 mm in length from base of receptacle to end of bud. Bud diameter is 11 mm.
- *Bud form*.—Ovoid.
- *Bud color*.—As sepals divide petals are Red Group 47B.
- *Sepal inner surface*.—Color: Yellow-Green Group 145B. Surface: Lightly pubescent.
- *Sepal outer surface*.—Color: Yellow-Green Group 144A. Texture: Smooth.
- *Sepal shape*.—Apex: Cirrhose. Base: Flat at union with receptacle.
- *Sepal margin*.—Margins have no foliaceous appendages.
- *Sepal size*.—28 mm long, 9 mm wide.
- *Receptacle*.—Texture: Smooth. Size: 8 mm in height, 6 mm wide. Color: Yellow-Green Group 144A. Shape: Long funnel.
- *Pedicel*.—Surface: Smooth with stipitate glands. Length: About 45 mm. Diameter: 2 mm on average. Color: Yellow-Green Group 144A. Strength: Strong.
- *Peduncle*.—Length: 55 to 65 mm. Diameter: About 3 mm. Color: Yellow-Green Group 144A. Texture: Smooth.

Flower bud development: Flower buds are borne in clusters of 5 to 9flower buds per stem.

Flower bloom:

- *Fragrance*.—Strong, sweet perfume.
- *Duration*.—The blooms have a duration on the plant of approximately 18 days. Petals fall cleanly away from plant after flowers have fully matured.
- *Size*.—Flower diameter is 80 mm when open. Flower depth is 45 mm.
- *Flower shape*.—Cup shaped with a center that is tightly closed.
- *Shape of flower, side view*.—The upper portion is nearly flat and the lower portion is flat.

Petalage: Under normal conditions, flowers have. about 55 petals.

General tonality of flower: Open flowers are Yellow Group 8C and Red-Purple Group 58B.

Petal color:

- *Upon opening, outer & inner petals*.—Upper surface: Basal zone Yellow Group 8A. Middle zone Yellow Group 8C. Streaks of Red- Purple Group 58B. Lower surface: Yellow Group 8D streaked with Red-Purple Group 61D.
- *Basal petal spots, upon opening*.—Upper surface: Yellow Group 8A. Lower surface: None.
- *After opening, outer and inner petals*.—Upper surface: Yellow Group 8C with streaks of Red-Purple Group 58B. Lower surface: Yellow Group 8D with streaks of Red-Purple Group 58C.

Petals:

- *Petal reflex*.—Light bilateral reflex.
- *Margin*.—Entire and uniform. No undulations.
- *Shape*.—Broad and elliptic. Apex shape: Rounded. Base shape: Obtuse.
- *Size*.—About 37 mm (l)×40 mm (w).
- *Texture*.—Smooth.
- *Thickness*.—Average.

Petaloids:

- *Size*.—25 mm (l) by 20 mm (w).
- *Quantity*.—About 10.
- *Shape*.—The base is acute and the apex is rounded with a small cleft in the margin.
- *Color*.—The upper side is Yellow Group 8A and Red Group 45B. Lower surface is Yellow Group 8C with Red Group 47C.

Reproductive flower parts:

- *Pollen*.—None observed.
- *Anthers*.—Size: 2 mm in length. Color: Yellow Group 8D. Quantity: 60 on average.
- *Filaments*.—Color: Yellow Group 9B. Length: 8 mm.
- *Pistils*.—Length: 6 mm. Quantity: 45 on average.
- *Stigmas*.—Color: Greyed-Yellow Group 160 A.
- *Styles*.—Color: Red-Purple Group 61B.
- *Location of stigmas*.—Inferior in location relative to the length of the filaments and the height of the anthers.
- *Hips*.—None Observed.

PLANT

Plant growth: Upright. Plants are 40 to 46 cm in height, and 40 cm wide.

Stems:

- *Color of juvenile growth*.—Yellow-Green Group 144B.
- *Color of mature growth*.—Yellow-Green Group 144A.
- *Length*.—Canes are about 28 cm from the base of the plant of the flowering portion.
- *Diameter*.—About 3 mm.
- *Internodes*.—On mature canes about 35 mm between nodes.
- *Surface texture*.—Young wood: Smooth. Older wood: Smooth.

Long prickles:

- *Incidence*.—2 or 3 prickles per 10 cm of stem.
- *Size*.—Average length of prickles on mature stems is 6 mm.
- *Shape*.—Upper portion is linear. Lower portion is linear.

*Color*.—Juvenile prickles: Greyed-Yellow Group 160A. Mature prickles: Greyed-Orange Group 174B.

Plant foliage:

*Compound leaf*.—About 125 mm (l)×80 (w).

*Quantity*.—2 or 3 leaves per 10 cm of stem on average.

*Leaf bearing angle to the stem*.—45 degrees.

*Color of juvenile foliage*.—Upper side: Yellow-Green Group 144A with marginal intonations of Greyed-Purple Group 183B. Lower side: Yellow-Green Group 144B shade with Greyed-Purple Group 183C.

*Color of mature foliage*.—Upper side: Yellow-Green Group 147A. Lower side: Yellow-Green Group 146B.

Plant leaves and leaflets:

*Stipules*.—Size: 5 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm. Upper surface color: Yellow-Green Group 144A. Lower surface color: Yellow-Green Group 144A.

*Rachis*.—Length: About 50 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 54 mm long, 35 mm wide. Shape: Generally rounded. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah124' substantially as described and illustrated herein.

* * * * *